US012788902B2

(12) United States Patent
Hogan

(10) Patent No.: US 12,788,902 B2
(45) Date of Patent: Nov. 10, 2026

(54) METHOD OF PRODUCING AN APERTURE PLATE FOR A NEBULIZER

(71) Applicant: Stamford Devices Limited, Dangan (IE)

(72) Inventor: Brendan Hogan, Gort (IE)

(73) Assignee: Stamford Devices Limited, Galway (IE)

( * ) Notice: Subject to any disclaimer, the term of this patent is extended or adjusted under 35 U.S.C. 154(b) by 855 days.

(21) Appl. No.: 18/314,637

(22) Filed: May 9, 2023

(65) Prior Publication Data

US 2024/0001048 A1 Jan. 4, 2024

Related U.S. Application Data

(63) Continuation of application No. 16/686,286, filed on Nov. 18, 2019, now Pat. No. 11,679,209, which is a (Continued)

(51) Int. Cl.

*A61M 11/00* (2006.01)
*B05B 17/00* (2006.01)
(Continued)

(52) U.S. Cl.

CPC ......... *A61M 11/003* (2014.02); *A61M 11/005* (2013.01); *C25D 1/08* (2013.01);
(Continued)

(58) Field of Classification Search

CPC ..... A61M 11/003; A61M 11/005; C25D 1/08; C25D 7/00; C25D 3/567; C25D 3/50; C25D 3/56; B05B 17/0646; B05B 17/00
See application file for complete search history.

(56) References Cited

U.S. PATENT DOCUMENTS 2,226,706 A 12/1940 Cawein
3,130,487 A 4/1964 Mears
(Continued)

FOREIGN PATENT DOCUMENTS

CN 1149907 A 5/1997
DE 1948135 A1 4/1971
(Continued)

OTHER PUBLICATIONS

International Preliminary Report on Patentability, Written Opinion and International Search Report for corresponding International Application No. PCT/EP2011/067106 dated Jun. 4, 2013 (19 pages).
(Continued)

*Primary Examiner* — Victoria Murphy
(74) *Attorney, Agent, or Firm* — Bookoff McAndrews, PLLC

(57) ABSTRACT

A photo-resist (21) is applied in a pattern or vertical columns having the dimensions of holes or pores of the aperture plate to be produced. This mask pattern provides the apertures which define the aerosol particle size, having up to 2500 holes per square mm. There is electro-deposition of metal (22) into the spaces around the columns (21). There is further application of a second photo-resist mask (25) of much larger (wider and taller) columns, encompassing the area of a number of first columns (21). The hole diameter in the second plating layer is chosen according to a desired flow rate.

18 Claims, 6 Drawing Sheets

Related U.S. Application Data continuation of application No. 14/401,480, filed as application No. PCT/EP2013/060803 on May 24, 2013, now Pat. No. 10,512,736.

(60) Provisional application No. 61/658,054, filed on Jun. 11, 2012.

(51) Int. Cl.
*C25D 1/08* (2006.01)
*C25D 3/56* (2006.01)
*C25D 7/00* (2006.01)

(52) U.S. Cl.
CPC ............ *C25D 7/00* (2013.01); *B05B 17/0646* (2013.01); *C25D 3/567* (2013.01)

(56) References Cited

U.S. PATENT DOCUMENTS

| | | | |
|---|---|---|---|
| 3,325,319 A | 6/1967 | Frantzen | |
| 4,184,925 A | 1/1980 | Kenworthy | |
| 4,379,737 A | 4/1983 | Mearig | |
| 4,430,784 A | 2/1984 | Brooks et al. | |
| 4,773,971 A | 9/1988 | Lam et al. | |
| 4,839,001 A | 6/1989 | Bakewell | |
| 4,849,303 A | 7/1989 | Graham et al. | |
| 4,972,204 A | 11/1990 | Sexton | |
| 5,152,456 A | 10/1992 | Ross et al. | |
| 5,164,740 A | 11/1992 | Ivri | |
| 5,180,482 A | 1/1993 | Abys et al. | |
| 5,373,629 A | 12/1994 | Hupe et al. | |
| 5,487,378 A | 1/1996 | Robertson et al. | |
| 5,560,837 A | 10/1996 | Trueba | |
| 5,565,113 A | 10/1996 | Hadimioglu et al. | |
| 5,586,550 A | 12/1996 | Ivri et al. | |
| 5,646,662 A | 7/1997 | Kitahara | |
| 5,685,491 A | 11/1997 | Marks et al. | |
| 5,758,637 A | 6/1998 | Ivri et al. | |
| 5,766,441 A | 6/1998 | Arndt et al. | |
| 5,837,960 A | 11/1998 | Lewis et al. | |
| 5,899,390 A | 5/1999 | Arndt et al. | |
| 5,921,474 A | 7/1999 | Zimmermann et al. | |
| 5,976,342 A | 11/1999 | Arndt et al. | |
| 6,050,507 A | 4/2000 | Holzgrefe et al. | |
| 6,074,543 A | 6/2000 | Yoshihira et al. | |
| 6,205,999 B1 | 3/2001 | Ivri et al. | |
| 6,230,992 B1 | 5/2001 | Arndt et al. | |
| 6,310,641 B1 | 10/2001 | Mrvos et al. | |
| 6,357,677 B1 | 3/2002 | Ren et al. | |
| 6,586,112 B1 | 7/2003 | Te | |
| 6,605,866 B1 | 8/2003 | Crowley et al. | |
| 6,773,094 B2 | 8/2004 | Linliu et al. | |
| 7,066,398 B2 | 6/2006 | Borland et al. | |
| 7,104,475 B2 | 9/2006 | Goenka et al. | |
| 7,259,640 B2 | 8/2007 | Brown et al. | |
| 7,442,303 B2 | 10/2008 | Jacobson | |
| 8,398,001 B2 | 3/2013 | Borland et al. | |
| 2002/0063751 A1 | 5/2002 | Aizawa et al. | |
| 2002/0157956 A1 | 10/2002 | Ikeda | |
| 2003/0231227 A1 | 12/2003 | Kim | |
| 2004/0035413 A1 | 2/2004 | Smaldone et al. | |
| 2005/0263608 A1 | 12/2005 | Ivri | |
| 2006/0055739 A1 | 3/2006 | Kim et al. | |
| 2006/0086689 A1 | 4/2006 | Raju et al. | |
| 2006/0203036 A1 | 9/2006 | Sexton et al. | |
| 2007/0212653 A1 | 9/2007 | Hori | |
| 2007/0277816 A1 | 12/2007 | Morrison et al. | |
| 2008/0023572 A1 | 1/2008 | Clark | |
| 2009/0053174 A1 | 2/2009 | Kaneko et al. | |
| 2010/0055045 A1 | 3/2010 | Gerhart et al. | |
| 2010/0282247 A1 | 11/2010 | Kadrichu et al. | |
| 2010/0319694 A1 | 12/2010 | Cook et al. | |
| 2013/0334338 A1* | 12/2013 | Hogan | A61M 11/003 239/548 |
| 2013/0334339 A1 | 12/2013 | Xu | |
| 2015/0336115 A1 | 11/2015 | Hogan et al. | |
| 2016/0130715 A1 | 5/2016 | Xu | |

FOREIGN PATENT DOCUMENTS

| | | | |
|---|---|---|---|
| DE | 2050285 A1 | 5/1972 | |
| DE | 19527846 | 1/1997 | |
| EP | 0683048 A2 | 11/1995 | |
| EP | 1 199 382 A1 | 4/2002 | |
| EP | 1810743 | 7/2007 | |
| EP | 2204238 A1 | 7/2010 | |
| EP | 2886185 A1 * | 6/2015 | B01D 71/02232 |
| GB | 2240494 A | 8/1991 | |
| GB | 2524337 | 9/2015 | |
| JP | 4-183892 | 6/1992 | |
| JP | H 04-322290 | 11/1992 | |
| JP | H 05-239682 | 9/1993 | |
| JP | H 05-74669 | 10/1993 | |
| JP | 10-507243 | 7/1998 | |
| JP | 10-228114 | 8/1998 | |
| JP | H 11138827 | 5/1999 | |
| JP | 2002019125 | 1/2002 | |
| JP | 2002-166541 | 6/2002 | |
| JP | 2002187374 A | 7/2002 | |
| JP | 2002-289097 | 10/2002 | |
| JP | 2004-290426 A | 10/2004 | |
| JP | 2006-056151 | 3/2006 | |
| JP | 2006-150093 A | 6/2006 | |
| JP | 20060297688 | 11/2006 | |
| JP | 7-329304 | 12/2007 | |
| JP | 2008-545525 | 12/2008 | |
| JP | 2009-195669 A | 9/2009 | |
| JP | 2010-540526 A | 12/2010 | |
| RU | 2078405 | 4/1997 | |
| WO | WO 91/03920 A2 | 3/1991 | |
| WO | WO 01/18280 A1 | 3/2001 | |
| WO | WO 01/071065 | 3/2001 | |
| WO | WO 2006/127181 | 11/2006 | |
| WO | WO 2010/134967 A1 | 11/2010 | |
| WO | WO 2011/039233 A1 | 4/2011 | |
| WO | WO 2011/083380 A1 | 7/2011 | |
| WO | WO 2012/092163 A | 7/2012 | |
| WO | WO-2012092163 A1 * | 7/2012 | B05B 17/0646 |
| WO | WO 2013/186031 A | 12/2013 | |

OTHER PUBLICATIONS

Vecellio, L., "The mesh nebulizer: a recent innovation for aerosol delivery," Breathe, vol. 2, No. 3, Mar. 2006 (10 pages).

International Preliminary Report on Patentability and Written Opinion for corresponding International Application No. PCT/EP2013/060803 dated Dec. 16, 2014 (9 pages).

* cited by examiner

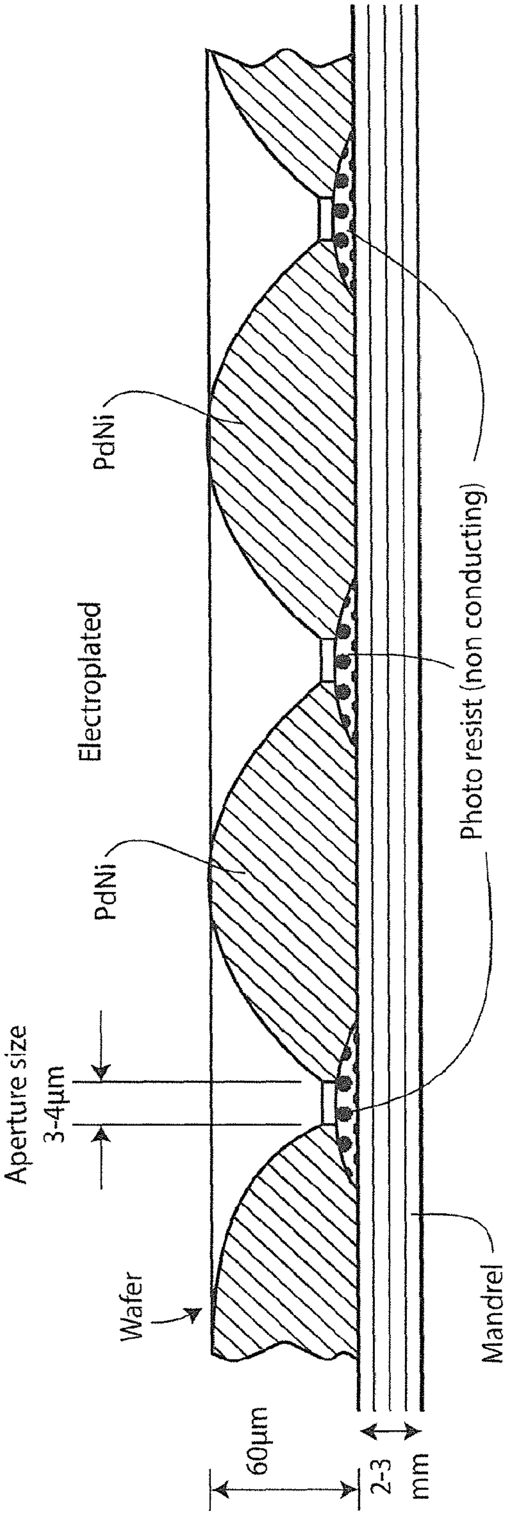
Fig.1 (Prior Art)
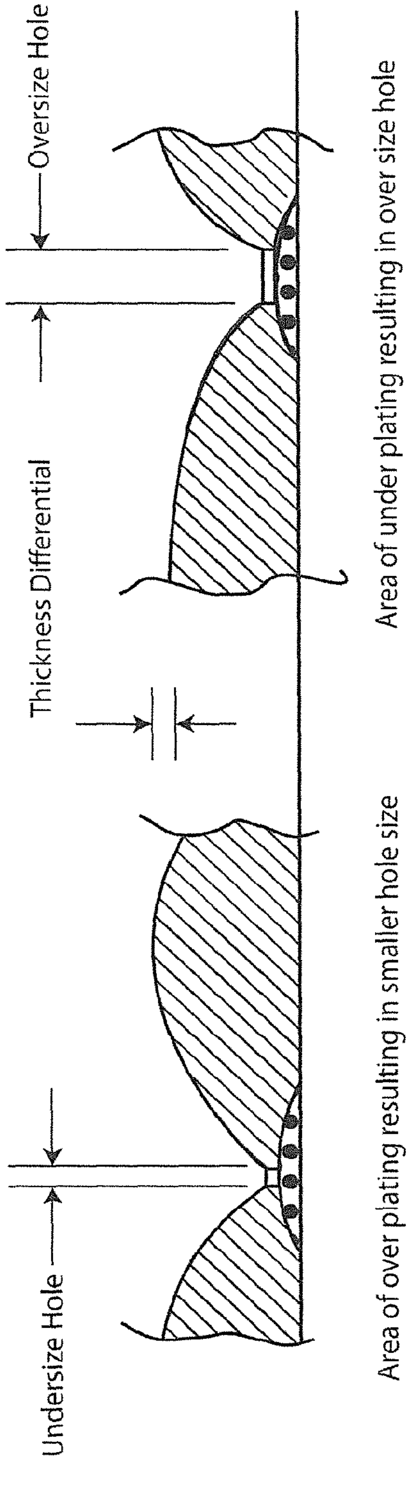
Fig.2 (Prior Art)
Fig.3 (Prior Art)

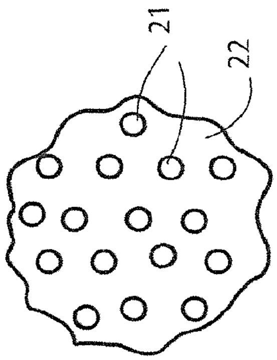
Fig.5 Part Plan View
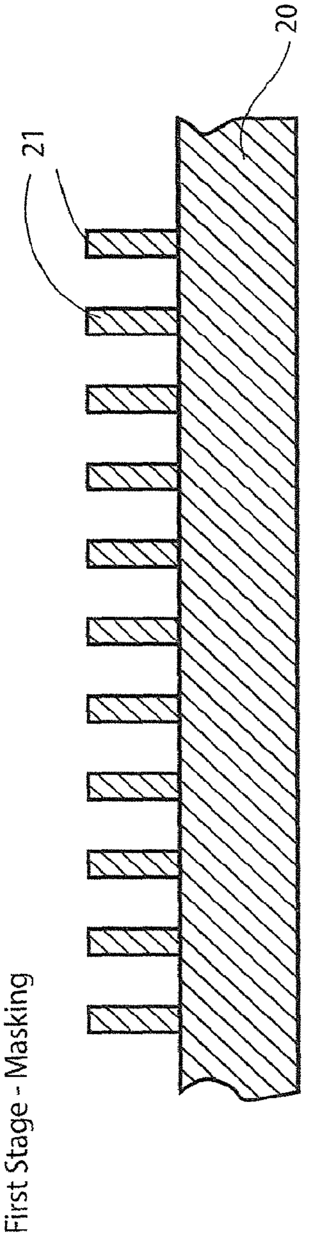
First Stage - Masking
Fig.4(a)
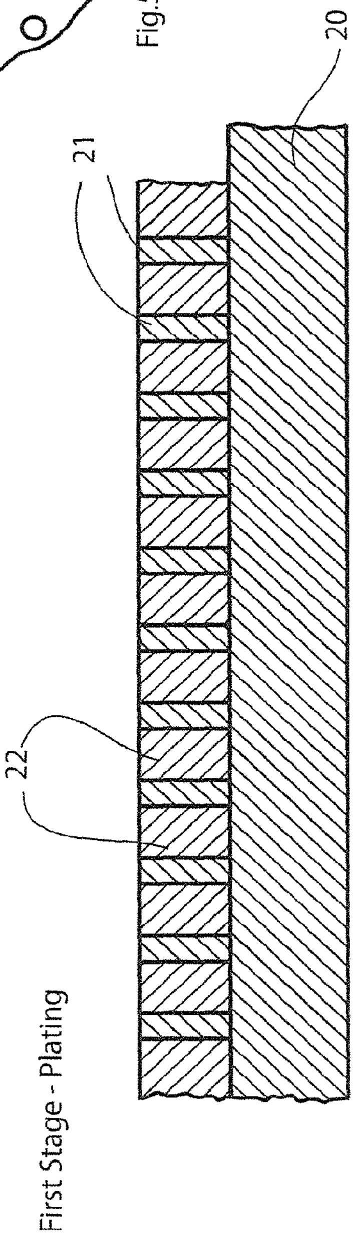
First Stage - Plating
Fig.4(b)

Second Stage - Masking

Second Stage - Plating

First Stage - Masking

First Stage - Plating

Part Plan View

METHOD OF PRODUCING AN APERTURE PLATE FOR A NEBULIZER

CROSS-REFERENCE TO RELATED APPLICATIONS

This application is a continuation of U.S. application Ser. No. 16/686,286, filed Nov. 18, 2019, which is a continuation of U.S. application Ser. No. 14/401,480, filed Nov. 14, 2014, now U.S. Pat. No. 10,512,736, which is a National Stage filing under 35 U.S.C. § 371 of International Application No. PCT/EP2013/060803, filed May 24, 2013, which claims priority to U.S. Provisional Application No. 61/658,054, filed Jun. 11, 2012, the contents of each of which are incorporated herein by reference in their entireties.

INTRODUCTION

The invention relates to manufacture of aperture plates for aerosol (or “nebulizer”) devices. Vibrating aperture plates are used in a wide range of aerosol devices, and are typically supported around their rims by a vibrating support which is vibrated by a piezo element. Also, aerosol devices may have passive or static aperture plates, which operate for example by an acoustic signal from a horn causing a stream of medication to be filtered through the aperture plate.

An aperture plate is used for aerosol delivery of liquid formulations delivering a controlled liquid droplet size suitable for pulmonary drug delivery. The ideal nebulizer is one which assures a consistent and accurate particle size in combination with an output rate that can be varied to deliver the drug to the targeted area as efficiently as possible. Delivery of the aerosol to the deep lung such as the bronchi and bronchiole regions requires a small and repeatable particle size typically in the range of 2-4 μm. In general, outputs greater than 1 ml/min are required.

Currently, aperture plates are produced by a variety of different means, including electroplating and laser drilling. Electroplating is generally the most advantageous production method from a technical and economic standpoint. U.S. Pat. No. 6,235,177 (Aerogen) describes an approach based on electroplating, in which a wafer material is built onto a mandrel by a process of electro-deposition where the liquefied metals in the plating bath (typically Palladium and Nickel) are transferred from the liquid form to the solid form on the wafer. Material is transferred to the conducting surface on the mandrel and not to the photo resist areas which are non-conducting. Areas are masked with non-conductive photo resist where metallic build-up is not required, see FIG. 1. After the conclusion of the plating process, the mandrel/wafer assembly is removed from the bath and the wafer peeled from the mandrel for subsequent processing into an aperture plate.

However, a problem with this approach is that the hole size is dependent on the plating time and the thickness of the resulting wafer. The process can be difficult to control, and if not perfectly controlled some holes may be near closed or blocked as shown in FIG. 2, or over-sized as shown in FIG. 3, and there may be out-of-tolerance variation in the sizes of the holes Also, there are limitations on the number of holes per unit of area. Further, with this technology an increase in output rate usually requires an increase in particle size, which generally may not be desired. It is more desired to increase output rate without increasing particle size.

Combinations of hole size accuracy and number of holes per unit of area can be a significant determinant in the nebulizer output rate and resulting particle size distribution.

WO2011/139233 (Agency for Science, Technology and Research) describes a microsieve manufactured using SUS material with photo-masking.

U.S. Pat. No. 4,844,778 (Stork Veco) describes manufacture of a membrane for separating media, and a separation device incorporating such a membrane. The manufacturing method includes a two step photolithographic procedure.

EP 1199382 (Citizen watch Co. Ltd.) describes a production method for a hole structure in which there is exposure to photosensitive material in multiple cycles to provide deeper holes tapered towards the top because there is exposure through the first holes.

The invention is directed towards providing an improved method for manufacture of an aperture plate for a nebulizer to address the above problems.

SUMMARY OF THE INVENTION

According to the invention, there is provided a method of manufacturing an aerosol-forming aperture plate wafer, the method comprising:

- providing a mandrel of conductive material,
- applying a mask over the mandrel in a pattern of columns,
- electroplating the spaces around the columns,
- removing the mask to provide a wafer of the electroplated material with aerosol-forming holes where the mask columns were,
- wherein said masking and plating steps are followed by at least one subsequent cycle of masking and plating to increase the wafer thickness,
- wherein the at least one subsequent cycle brings the overall wafer thickness up to a level desired according to criteria for removal of the wafer from the mandrel, and/or desired frequency of operation of the aperture plate, and/or physical constraints of an aerosolizing drive,
- wherein the at least one subsequent cycle provides:
- spaces at least some of which overlie a plurality of aerosol-forming apertures, and
- a plating material which occludes some of the aerosol-forming apertures, and
- wherein the at least one subsequent cycle is performed according to desired flow rate through the aperture plate.

All of the mask of all cycles may be removed together in some embodiments, however, in other embodiments the mask of one cycle may be removed before the subsequent cycle of masking and plating, and if so the subsequent plating is more likely to at least partly in-fill some of the lower holes.

In one embodiment, the columns have a depth in the range of 5 μm to 40 μm, and preferably 15 μm to 25 μm. In some embodiments, the columns have a width dimension in the plane of the mandrel in the range of 1 μm to 10 μm, preferably 2 μm to 6 μm.

In one embodiment, the electroplating is continued until the plated material is substantially flush with the tops of the columns.

In one embodiment, there is substantially no overlap between the plated material and the mask material. In one embodiment, the at least one subsequent cycle brings the overall wafer thickness up to above 50 μm, and preferably greater than 58 sm. In one embodiment, the extent of occlusion in the or each subsequent cycle is chosen for desired mechanical properties of the aperture plate.

In one embodiment, the first masking and plating are performed so that the aerosol-forming holes are tapered in a funnel-shape.

In one embodiment, the subsequent masking and plating are performed so that the overlay spaces are tapered in a funnel shape.

In one embodiment, the plated metal includes Ni and/or Pd. In one embodiment, the Ni and/or Pd are present at a surface at a concentration chosen for anti-corrosion properties. In one embodiment, the proportion of Pd is in the range of 85% w/w and 93% w/w, and preferably about 89%, substantially the balance being Ni. In one embodiment, the plated material includes Ag and/or or Cu at a surface, at a concentration chosen for anti-bacterial properties.

In one embodiment, the method comprises the further steps of further processing the wafer to provide an aperture plate ready to fit into an aerosol-forming device. In one embodiment, the wafer is formed into a non-planar shaped aperture plate. In one embodiment, the wafer is formed into a shape with a configuration chosen according to desired aerosolizing spray angles. In one embodiment, the wafer is formed into a shape having an operative dome-shaped part and a flange for engaging a drive. In one embodiment, the wafer is annealed before being formed.

In another aspect, the invention provides an aperture plate wafer comprising a body of metal whenever formed in a method as defined above in any embodiment.

In a further aspect the invention provides an aperture plate whenever formed by a method as defined above in any embodiment.

In another aspect, the invention provides an aperture plate wafer comprising a bottom layer of photolithography-plated metal with aerosol-forming through holes and at least one top layer of photolithography-plated metal having spaces, in which said spaces overlie a plurality of aerosol-forming through holes, in which the size and number of aerosol-forming holes per large hole is related to a desired aerosol flow rate In one embodiment, the top layer occludes some of the holes in the bottom layer.

In one embodiment, the metal of all layers is the same.

In one embodiment, the plated metal includes Ni and/or Pd. In one embodiment, the Ni and/or Pd are present at a surface at a concentration chosen for anti-corrosion properties.

In one embodiment, the proportion of Pd is in the range of 85% w/w and 93% w/w, and preferably about 89%, substantially the balance being Ni. In one embodiment, the plated metal includes Ag and/or or Cu at a surface, at a concentration chosen for anti-bacterial properties.

In another aspect, the invention provides an aperture plate including a wafer as defined above in any embodiment.

In another aspect, the invention provides an aerosol-forming device comprising an aperture plate as defined above in any embodiment, and a drive engaging the plate to vibrate it at a desired frequency for forming an aerosol.

In another aspect, the invention provides an aerosol-forming device comprising an aperture plate as defined above in any embodiment, a support for the aperture plate for passive aperture plate use, and a horn arranged to force a wave of liquid through the aperture plate.

DETAILED DESCRIPTION OF THE INVENTION

The invention will be more clearly understood from the following description of some embodiments thereof, given by way of example only with reference to the accompanying drawings in which:—

FIGS. 1 to 3 are cross-sectional diagrams outlining a prior art process as described above;

FIGS. 4(*a*) and 4(*b*) are cross-sectional views showing masking and plating steps for a first stage of the method, and FIG. 5 is a part plan view of the wafer for this stage;

FIGS. 6(*a*) and 6(*b*) are cross-sectional views showing a second masking and plating stage, and FIG. 7 is a plan view;

Figure 6A:
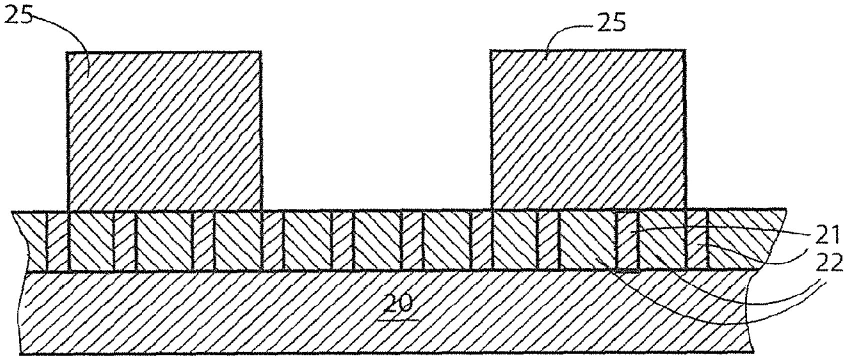
Figure 6B:
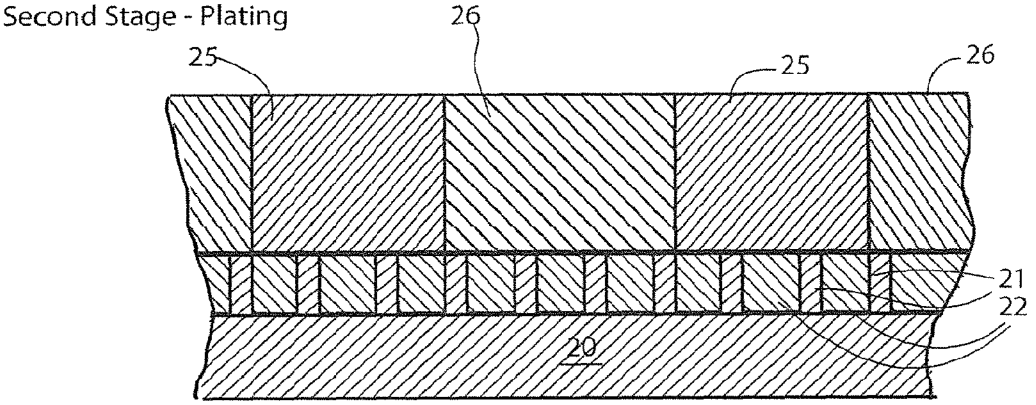
Figure 7:
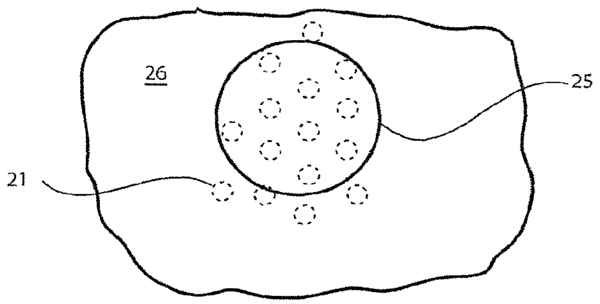
Figure 11A:
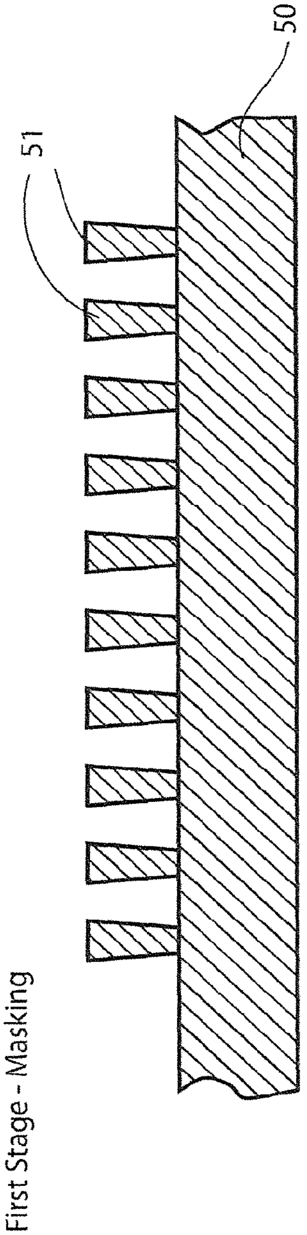
Figure 11B:
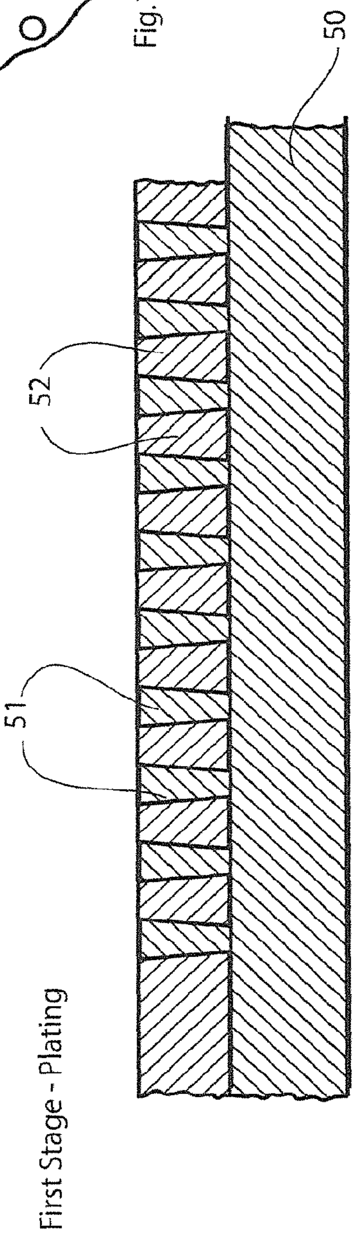
Figure 12:
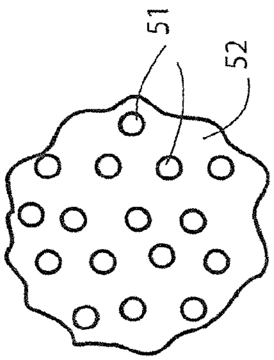
Figure 13A:
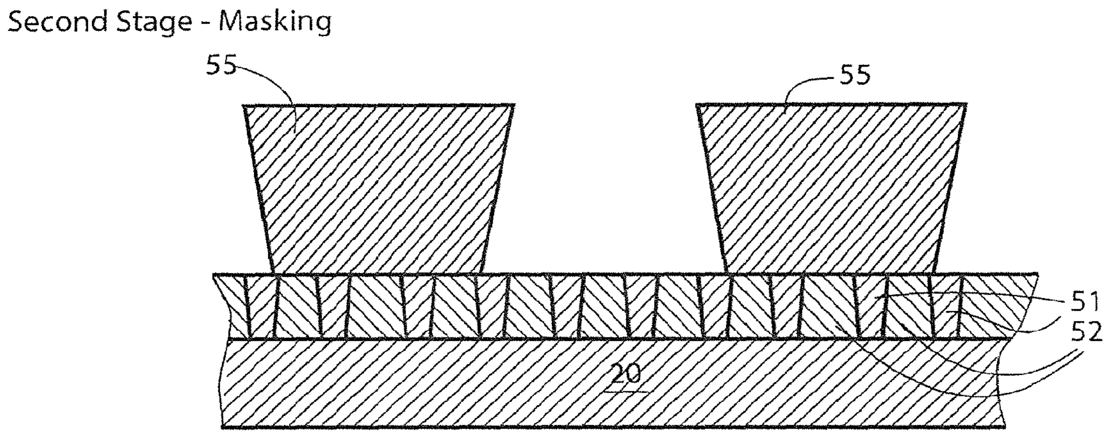
Figure 13B:
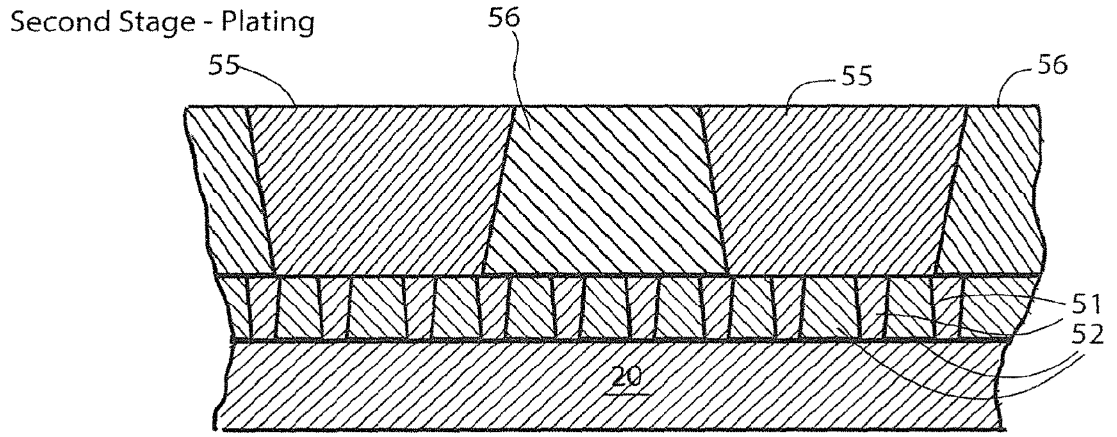
Figure 14:
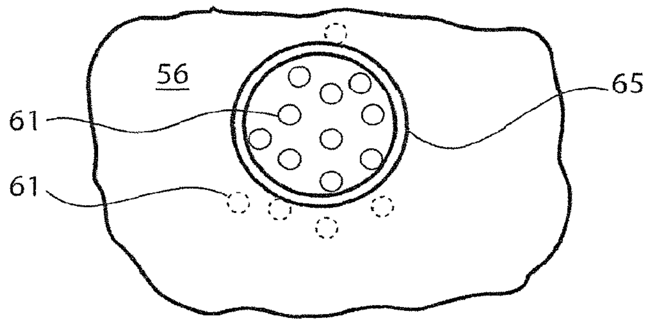

FIGS. 11(*a*), 11(*b*) and 12 are views equivalent to FIGS. 4(*a*), 4(*b*), and 5 for a second embodiment, in which the holes are tapered; and FIGS. 13(*a*) and 13(*b*) are views equivalent to FIGS. 6(*a*) and 6(*b*), and for the second embodiment, and FIG. 14 is a plan view in the region of one large upper hole after removal of the photo-resist mask.

Referring to FIG. 4(*a*) a mandrel 20 has a photo-resist 21 applied in a pattern of vertical columns having the dimensions of holes or pores of the aperture plate to be produced. The column height is preferably in the range of 5 μm to 40 μm height, and more preferably 5 μm to 30 μm, and most preferably 15 μm to 25 μm. The diameter is preferably in the range of 1 μm to 10 μm, and most preferably about 2 μm to 6 μm diameter. This mask pattern provides the apertures which define the aerosol particle size. They are much greater in number per unit of area when compared to the prior art; a twenty-fold increase is possible, thus having up to 2500 holes per square mm.

Referring to FIGS. 4(*b*) and 5 there is electro-deposition of metal 22 into the spaces around the columns 21.

As shown in FIG. 6(*a*) there is further application of a second photo-resist mask 25, of much larger (wider and taller) columns, encompassing the area of a number of first columns 21. The hole diameter in the second plating layer is between 20 μm and 400 μm and more preferably between 40 μm and 150 μm. To ensure higher flow rates this diameter is produced at the upper end of the range, and to assure lower flow rates it is produced at the lower end of the range to close more of the smaller openings on the first layer.

Figure 8:
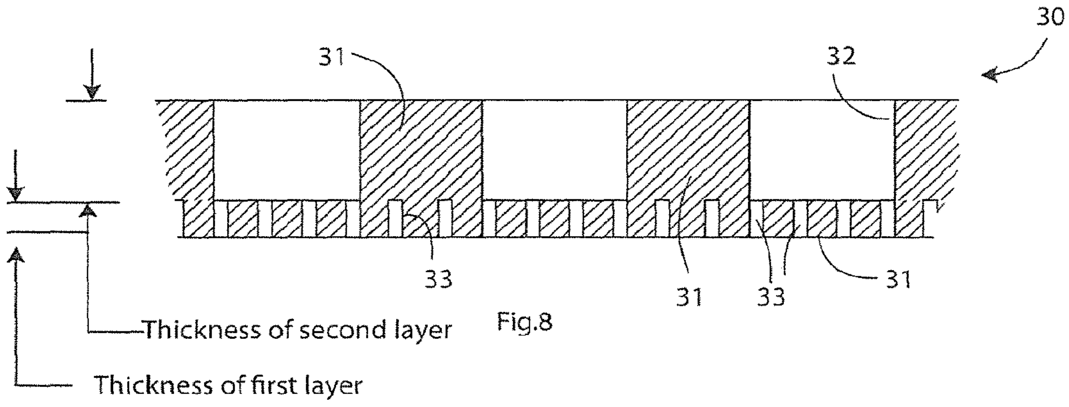
FIG. 8 is a cross-sectional view after resist removal.

Referring to FIGS. 6(*b*) and 7 the spaces around the photo-resist 25 are plated to provide a wafer body 26 on the mandrel 20. When the photo-resist 21 and 25 is cleaned with resist remover and rinsed away the plated material 22 and 26 is in the form of an aperture plate blank or mask 30, as shown in FIG. 8, having large top apertures 32 and small bottom apertures 33. In this embodiment all of the resist 21 and 25 is removed together, however, it is envisaged that the resist 21 may be removed before the subsequent cycle of masking and plating. In this case the subsequent plating is more likely to at least partly in-fill some of the aerosol-forming apertures.

Figure 9:
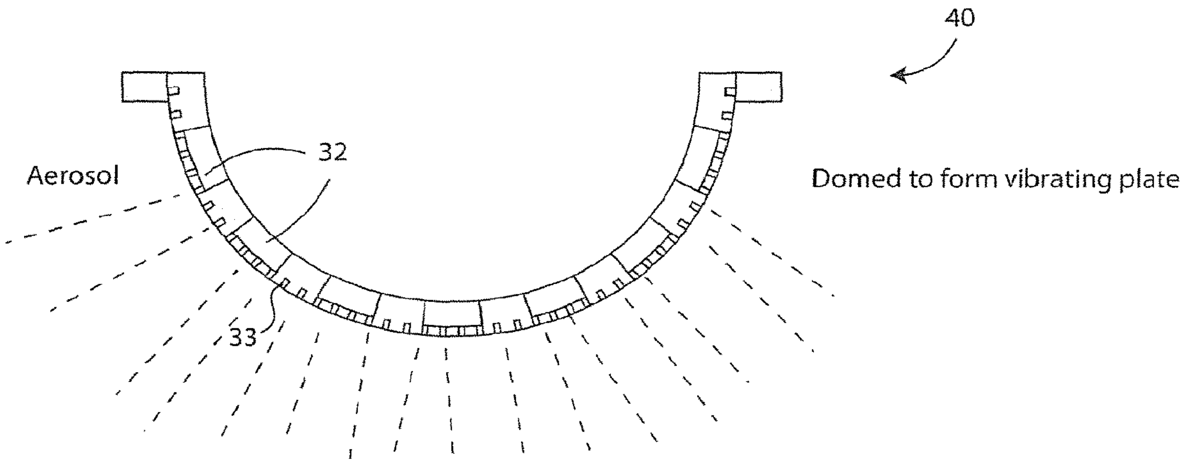
FIG. 9 shows the wafer after punching to form the final aperture plate shape.

As shown in FIG. 9 the wafer 30 is punched into a disc and is formed into a dome shape to provide a final product aperture plate 40.

At this stage the doming diameter may be selected to provide a desired spray angle and/or to set the optimum natural frequency for the drive controller. The dome shape provides a funnelling effect, and the particular shape of the domed plate affects the spray characteristics.

In an alternative embodiment the aperture plate is not domed, but is left planar, suitable for use in a device such as a passive plate nebulizer. In this type of nebulizer a sonotrode or horn is placed in contact with the medication on the plate. A piezo element causes rapid movement of the transducer horn, which forces a wave of medication against the aperture plate causing a stream of medication to be filtered through the plate to the exit side as an aerosol.

The majority of the benefits of the aperture plate manufacture of the invention are applicable to either vibrating or passive devices.

In more detail, the mandrel 20 is coated with the photo resist 21 with a column height and width equal to the target hole dimension. This coating and subsequent ultraviolet (UV) development is such that columns 21 of photo-resist are left standing on the mandrel 20. These columns are of the required diameter and are as high as their rigidity will support. As the columns are only less than 10 μm, and preferably less than 6 μm in diameter it is possible to get many more columns and resulting holes per unit of area than in the prior art. It is expected that there may be as many as twenty times more holes than in the prior art electroplating approach. This creates potential for a substantial increase in the proportion of open area and resultant nebulizer output.

The mandrel 20 with the selectively developed photo resist in the form of upstanding columns 21 is then placed in the plating bath and through the process of electro-deposition containing the metals Palladium Nickel (PdNi) in liquid form typically is then imparted to the surface. The plating activity is stopped when the height of the columns is reached. No over-plating is allowed as the plating is stopped just as it reaches the height of the columns of photo resist. The plating solution is chosen to suit the desired aperture plate dimensions and operating parameters such as vibration frequency. The Pd proportion may be in the range of about 85% to 93% w/w, and in one embodiment is about 89% w/w, the balance being substantially all Ni. The plated structure preferably has a fine randomly equiaxed grain microstructure, with a grain size from 0.2 μm to 2.0 μm for example. Those skilled in the electro-deposition field art will appreciate how plating conditions for both plating stages may be chosen to suit the circumstances, and the entire contents of the following documents are herein incorporated by reference: U.S. Pat. Nos. 4,628,165, 6,235,117, US2007023547, US2001013554, WO2009/042187, and Lu S. Y., Li J. F., Zhou Y. H., "Grain refinement in the solidification of undercooled Ni—Pd alloys". Journal of Crystal Growth 309 (2007) 103-111, Sep. 14, 2007. Generally, most electroplating solutions involving Palladium and Nickel would work or Nickel only or indeed Phosphorous & Nickel (14:86) or Platinum. It is possible that a non-Palladium wafer could be plated at the surface (0.5 to 5.0 μm thick, preferably 1.0 to 3.0 μm thick) in PdNi to impart more corrosion resistance. This would also reduce the hole sizes if smaller openings were desired.

When removed from the plating bath, the wafer thickness is typically 5-40 μm depending on the height of the columns. Peeling off the wafer at this point would yield a very thin wafer in comparison to the standard 60 μm thickness of the prior art. A wafer of this thickness would lack rigidity, be very difficult to process, and would require complex and expensive changes to the mechanical fabrication of the nebulizer core to achieve a natural frequency equivalent to the state of the art such that the existing electronic control drivers would be useable, which in some cases are integrated into ventilators. Use of a different drive controller would be a significant economic barrier to market acceptance due to the costs involved.

This problem is overcome by offering the plated mandrel to the second photo resist deposition process. In one embodiment, the photo resist thickness is placed to a depth equal to that required to bring the overall wafer thickness to approximately 60 μm (similar to the prior art wafer thickness). The second mask height is preferably in the range of 40-50 μm for many applications. It is then developed to allow larger columns to stand on the plated surface. These are typically of a diameter between 40-100 μm but could be larger or smaller. The additional height from the second plating aids removal from the mandrel, but importantly it also achieves a particular thickness which is equivalent to the prior art aperture plate thickness to allow the end product aperture plate 40 to be electrically driven by the existing controllers on the market. This creates a natural frequency matching to achieve correct vibration to generate an aerosol. In general, the second plating stage provides a thickness more suited to the nebulizer application for rigidity, flexibility and flexural strength. Another aspect is that it occludes some of the smaller holes, thereby achieving improved control over flow rate. Hence, the second masking and plating stage can be used to "tune" the end product aperture plate according to desired flow rate. Also, it may be rapidly changed between small batches to enable a wide range of differently tuned plates.

The wafer is then carefully peeled from the substrate without the aid of any subsequent processes such as etching or laser cutting. This ease of peeling has the advantages of not imparting additional mechanical stresses into an already brittle wafer. The wafer is then washed and rinsed in photo-resist remover prior to metrology inspection.

In the aperture plate blank or mask 30 the holes 33 have a depth equal to the first plating layer and the final wafer thickness will be equal to the sum of both plating layers, see FIGS. 8 and 9. It is then ready for annealing, punching and doming to form the vibrating plate 40 shown in FIG. 9.

There may be additional steps to improve the membrane properties for certain applications. For example, the membrane may be of an electroformed Ni substrate material that is over-plated with corrosion-resistant materials such as Copper, Silver, Palladium, Platinum and/or PdNi alloys. Copper and silver advantageously have bacteria-resistant properties.

It will be appreciated that the invention provides an aperture plate having a first layer of electroformed metal with a plurality of aerosol-forming through holes which defines the droplet size being ejected and a second top layer of similar or dis-similar electroformed material with larger diameter holes or spaces above the aerosol-forming holes and the plating material of which occlude some of the first layer holes.

In various embodiments, the second layer has a number of holes or spaces with diameters chosen such that a predetermined number of droplet size forming first layer holes are exposed, which determines the number of active holes and thus defines the quantity of liquid being aerosolised per unit of time The size and number of holes in both layers can be independently varied to achieve the desired ranges of droplet size and flow rate distribution, which is not possible with the prior art plating defined technology.

It will also be appreciated that the invention provides the potential for a much greater number of holes per unit of area when compared to the prior art. For example a twenty-fold increase is possible, thus having up to 2500 holes per square mm.

Also, in various embodiments the second layer at least completely or partly inter-fills some of the aerosol-forming holes in the first layer, thus forming mechanical anchorage of both layers to help achieve endurance life requirements.

The following is a table of examples of different hole configurations for aperture plates ("AP") of 5 mm diameter:

| | | | | |
|---|---|---|---|---|
| Large Hole Diameter (mm) | 0.10 | 0.08 | 0.06 | 0.04 |
| Number Large Holes/AP | 815 | 1085 | 1464 | 2179 |
| Small Holes/Large Hole | 12 | 7 | 4 | 1 |
| Small Holes/AP | 9780 | 7595 | 5856 | 2179 |

Advantageous aspects of the invention include:

(i) Greater number of holes per unit of area are possible (ii) Smaller and more diametrically accurate hole sizes are possible.

(iii) Similar thickness to existing commercially available wafers, which alleviates the onerous need to re-design the nebulizer to match the correct frequency for the existing controllers to activate the aerosol generator.

(iv) Only two plating layers or plating steps are required (v) Still easy to carefully peel the wafer from the mandrel substrate.

(vi) Possible to use existing electronic controllers to drive the aperture plate as the natural frequencies are matched, having achieved similar aperture plate thickness.

(vii) Possible to get smaller and more controllable particle sizes (2-4 μm).

(viii) Possible to achieve higher flow rates (0.5 to 2.5 ml/min, more typically 0.75-1.5 ml/min)

Figure 10:
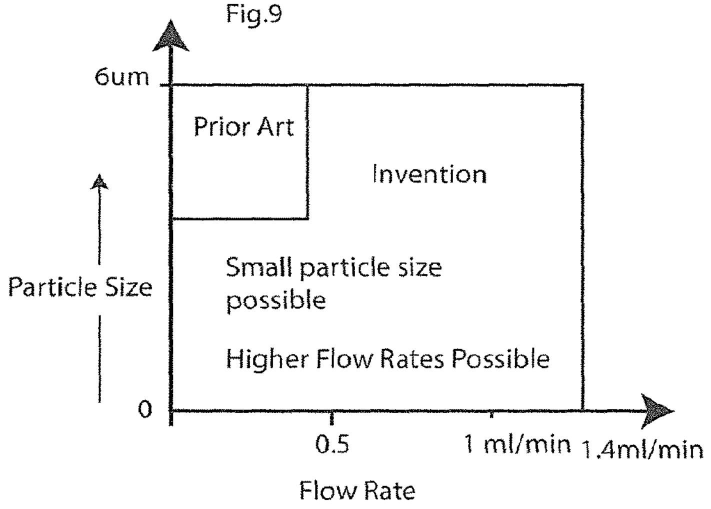
FIG. 10 is a plot of particle size vs. flow rate to illustrate operation of the aperture plate.

(ix) Possible to achieve flow rates and particle size more independent of each other when compared to the prior art as described. (Typically in the prior art, the increasing flow rate usually requires increasing particle size and vice versa). These advantages are illustrated in the plot of FIG. 10.

Referring to FIGS. 1I to 14 in a second embodiment the processing is much the same as for the above embodiment. In this case however, both of the sets of photo-resist columns are tapered so that the resultant holes are tapered for improved flow of aerosol liquid. There is a mandrel 50, first mask columns 51 and in-between plating 52. The second mask comprises tapered columns 55, and the spaces in-between are plated with metal 56. Greater care is required for the plating steps to ensure that there is adequate plating under the mask overhangs. FIG. 14 shows a plan view, in this case after removal of the photo resist. It will be seen that there are several small holes 61 for each large top hole 65 in the PdNi body 56/52. The top hole 65 has the effect of a funnel down to the small holes 61, which themselves are funnel-shaped.

The invention is not limited to the embodiments described but may be varied in construction and detail. For example, it is envisaged that the second cycle of masking and plating may not be required if the wafer can be removed from the mandrel, either due to the required wafer depth being achieved in the first stage or due to improved wafer-removal technologies being available. In addition, a third layer could be applied to provide more mechanical rigidity to the aperture plate. Also, in the embodiments described above the layers are of the same metal. However it is envisaged that they may be different, and indeed the metal within each hole-forming layer may include sub-layers of different metals. For example the composition at one or both surfaces may be different for greater corrosion resistance and/or certain hydrophilic or hydrophobic properties. Also, there may be an additional plating step for the top 1 to 5 μm or 1 to 3 μm surface layer.

The invention claimed is:

1. A method of manufacturing an aerosol-forming aperture plate wafer, the method comprising:

providing a mandrel of conductive material, applying a mask over the mandrel in a pattern of columns, electroplating around the columns, and removing the mask to provide a wafer of the electroplated material with aerosol-forming holes where the mask columns were, wherein said masking and plating steps are followed by at least one subsequent cycle of masking and plating to increase the wafer thickness, wherein the at least one subsequent cycle brings the overall wafer thickness up to a level desired according to criteria for removal of the wafer from the mandrel, and/or desired frequency of operation of the aperture plate, and/or physical constraints of an aerosolizing drive, wherein the at least one subsequent cycle provides after mask removal:

spaces at least some of which overlie a plurality of aerosol-forming apertures, and a plating material which occludes some of the aerosol-forming apertures, and wherein the at least one subsequent cycle is performed according to desired flow rate through the aperture plate.

2. The method as claimed in claim 1, wherein the columns have a depth in the range of 5 μm to 40 μm.

3. The method as claimed in claim 1, wherein the columns have a width dimension in the plane of the mandrel in the range of 1 μm to 10 μm.

4. The method as claimed in claim 1, wherein the electroplating is continued until the plated material is substantially flush with the tops of the columns.

5. The method as claimed in claim 1, wherein there is substantially no overlap between the plated material and the mask material.

6. The method as claimed in claim 1, wherein the at least one subsequent cycle brings the overall wafer thickness up to above 50 μm.

7. The method as claimed in claim 1, wherein the extent of occlusion in the or each subsequent cycle is chosen for desired mechanical properties of the aperture plate.

8. The method as claimed in claim 1, wherein the first masking and plating are performed so that the aerosol-forming holes are tapered in a funnel-shape.

9. The method as claimed in claim 1, wherein the subsequent masking and plating are performed so that the overlay spaces are tapered in a funnel shape.

10. The method as claimed in claim 1, wherein the plated metal includes Ni and/or Pd.

11. The method as claimed in claim 10, wherein the Ni and/or Pd are present at a surface at a concentration chosen for anti-corrosion properties.

12. The method as claimed in claim 11, wherein the proportion of Pd is in the range of 85% w/w and 93% w/w, substantially the balance being Ni.

13. The method as claimed in claim 1, wherein the plated material includes Ag and/or or Cu at a surface, at a concentration chosen for anti-bacterial properties.

14. The method as claimed in claim 1, comprising the further steps of further processing the wafer to provide an aperture plate ready to fit into an aerosol-forming device.

15. The method as claimed in claim 14, wherein the wafer is formed into a non-planar shaped aperture plate.

16. The method as claimed in claim 15, wherein the wafer is formed into a shape with a configuration chosen according to desired aerosolizing spray angles.

17. The method as claimed in claim 15, wherein the wafer is formed into a shape having an operative dome-shaped part and a flange for engaging a drive.

18. The method as claimed in claim 17, wherein the wafer is annealed before being formed.

* * * * *